(12) United States Patent
D'Amore et al.

(10) Patent No.: US 8,975,047 B2
(45) Date of Patent: Mar. 10, 2015

(54) PROCESS FOR MAKING ISOOCTENES FROM DRY 1-BUTANOL

(75) Inventors: Michael B. D'Amore, Wilmington, DE (US); Leo Ernest Manzer, Wilmington, DE (US); Edward S. Miller, Jr., Knoxville, TN (US); Jeffrey P. Knapp, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 2021 days.

(21) Appl. No.: 11/818,357

(22) Filed: Jun. 13, 2007

(65) Prior Publication Data
US 2008/0220488 A1 Sep. 11, 2008

Related U.S. Application Data (60) Provisional application No. 60/814,371, filed on Jun. 16, 2006.

(51) Int. Cl.
| | | |
|---|---|---|
| *C12P 9/00* | (2006.01) | |
| *C12P 5/02* | (2006.01) | |
| *C07C 1/20* | (2006.01) | |
| *C07C 5/03* | (2006.01) | |
| *C07C 9/21* | (2006.01) | |
| *C07C 29/04* | (2006.01) | |
| *C07C 41/06* | (2006.01) | |
| *C10L 1/06* | (2006.01) | |
| *C10L 1/16* | (2006.01) | |
| *C12P 7/04* | (2006.01) | |

(52) U.S. Cl.
CPC ... *C12P 5/02* (2013.01); *C07C 1/20* (2013.01); *C07C 5/03* (2013.01); *C07C 9/21* (2013.01); *C07C 29/04* (2013.01); *C07C 41/06* (2013.01); *C10L 1/06* (2013.01); *C10L 1/1608* (2013.01); *C12P 5/026* (2013.01); *C12P 7/04* (2013.01); *C07C 2521/08* (2013.01); *C07C 2527/054* (2013.01); *C07C 2529/18* (2013.01); *C07C 2529/40* (2013.01); *C07C 2531/08* (2013.01); *C07C 2531/10* (2013.01); *Y02E 50/343* (2013.01)
USPC ........................................................ 435/131

(58) Field of Classification Search
USPC ........................................................ 435/131
See application file for complete search history.

(56) References Cited

U.S. PATENT DOCUMENTS

| | | |
|---|---|---|
| 4,450,294 A | 5/1984 | Feldman |
| 4,628,116 A | 12/1986 | Cenedella |
| 5,192,673 A | 3/1993 | Jain et al. |
| 5,288,924 A | 2/1994 | Beech, Jr. et al. |
| 5,753,474 A | 5/1998 | Ramey |
| 5,755,967 A | 5/1998 | Meagher et al. |
| 6,358,717 B1 | 3/2002 | Blaschek et al. |
| 2002/0045786 A1 | 4/2002 | Gammersbach et al. |
| 2004/0054246 A1 | 3/2004 | Nierlich et al. |
| 2005/0054861 A1 | 3/2005 | Manzer |
| 2005/0089979 A1 | 4/2005 | Ezeji et al. |
| 2005/0112739 A1 * | 5/2005 | Golubkov ..................... 435/161 |

FOREIGN PATENT DOCUMENTS

GB 576480 * 4/1946

OTHER PUBLICATIONS

P. Gerhardt et al., Methods for General and Molecular Microbiology, 1994, Section 2 (Book—Available Upon Request).
U.S. Appl. No. 60/721,677, filed Sep. 29, 2005, Applicant: Gail K. Donaldson et al.
D. T. Jones, Clostridia, 2001, p. 125, John Wiley & Sons (Book—Available Upon Request).
T. G. Lenz et al., Economic Evaluation of the Acetone-Butanol Fermentation, Ind. Eng. Chem. Prod. Res. Dev., 1980, vol. 19:478-483.
D. Ramey et al., Final Report of Work Preformed Under U. S. Department of Energy DE-F-G02-00ER86106, pp. 57-58.
F. Liu et al., Separatiopn of Acetone-Butanol-Ethanol (ABE From Dilute Aqueous Solutions by Pervaporation, Separation and Purification Technology, 2005, vol. 42:273-282.
H. Scott Fogler, Elements of Chemical Reaction Engineering, Second Edition, 1992, Prentice-Hall Inc, CA (Book—Available Upon Request).
C. N. Satterfield, Heterogeneous Catalysis in Industrial Practice, Second Edition, Chapter 4, 1991, McGraw-Hill, New York (Book—Available Upon Request).
R. H. Perry et al., Perry's Chemical Engineer's Handbook, Seventh Edition, Section 13, 1997, McGraw-Hill, New York (Book—Available Upon Request).
R. L. Augustine, Heterogeneous Catalysis for the Synthetic Chemist, Section 3, 1996, Marcel Decker, New York (Book—Available Upon Request).

* cited by examiner

*Primary Examiner* — Ruth Davis (57) ABSTRACT

The present invention relates to a process for making isooctenes using dry 1-butanol derived from fermentation broth. The isooctenes so produced are useful for the production of fuel additives.

1 Claim, 8 Drawing Sheets

PROCESS FOR MAKING ISOOCTENES FROM DRY 1-BUTANOL

CROSS-REFERENCE TO RELATED APPLICATION

This application claims priority under 35 U.S.C. §119 from U.S. Provisional Application Ser. No. 60/814,371 (filed Jun. 16, 2006), the disclosure of which is incorporated by reference herein for all purposes as if fully set forth.

FIELD OF INVENTION

The present invention relates to a process for making isooctenes using dry 1-butanol obtained from fermentation broth.

BACKGROUND

Isooctenes are useful intermediates for the production of fuel additives. Isooctenes are typically produced from the reaction of isobutene or isobutene-containing hydrocarbon mixtures with an acid catalyst. U.S. Patent Application No. 2004/0054246, for example, describes the production of diisobutene from isobutene or mixtures comprising isobutenes using a solid acidic ion-exchange resin. U.S. Patent Application No. 2002/0045786 describes the preparation of diisobutylene from an isobutanol-containing raffinate using an acidic catalyst.

Efforts directed at improving air quality and increasing energy production from renewable resources have resulted in renewed interest in alternative fuels, such as ethanol and butanol, that might replace gasoline and diesel fuel. Efforts are currently underway to increase the efficiency of 1-butanol production by fermentative microorganisms utilizing renewable feedstocks, such as corn waste and sugar cane bagasse, as carbon sources. It would be desirable to be able to utilize such 1-butanol streams for the production of isooctenes, and for the further production of fuel additives from said isooctenes.

SUMMARY

The present invention relates to a process for making at least one isooctene comprising:

(a) obtaining a fermentation broth comprising 1-butanol;

(b) separating dry 1-butanol from said fermentation broth to form separated dry 1-butanol;

(c) contacting the separated dry 1-butanol of step (b), optionally in the presence of a solvent, with at least one acid catalyst at a temperature of about 50 degrees C. to about 450 degrees C. and a pressure from about 0.1 MPa to about 20.7 MPa to produce a reaction product comprising said at least one isooctene; and (d) recovering said at least one isooctene from said reaction product to obtain at least one recovered isooctene.

The expression "dry 1-butanol" as used in the present specification and claims denotes a material that is predominantly 1-butanol, but may contain small amounts of water (under about 5% by weight relative to the weight of the 1-butanol plus the water), and may contain small amounts of other materials, such as acetone and ethanol, as long as they do not materially affect the catalytic reaction previously described when performed with reagent grade 1-butanol.

The at least one recovered isooctene is useful as an intermediate for the production of transportation fuels and fuel additives. In particular, the at least one recovered isooctene can be converted to isooctanes, isooctanols or isooctyl alkyl ethers.

In an alternative embodiment, the reaction product produced by contacting 1-butanol with at least one acid catalyst can be used in subsequent reactions to produce compounds useful in transportation fuels without first recovering the at least one isooctene from the reaction product. The reaction product can be used to produce at least one isooctane by contacting the reaction product with at least one hydrogenation catalyst.

BRIEF DESCRIPTION OF THE DRAWING

The Drawing consists of eight figures.

DETAILED DESCRIPTION

The present invention relates to a process for making at least one isooctene from dry 1-butanol derived from fermentation broth. The at least one isooctene so produced is useful as an intermediate for the production of transportation fuels, wherein transportation fuels include, but are not limited to, gasoline, diesel fuel and jet fuel. The present invention further relates to the production of transportation fuel additives using isooctenes produced by the process of the invention.

More specifically, the present invention relates to a process for making at least one isooctene comprising contacting dry 1-butanol with at least one acid catalyst to produce a reaction product comprising at least one isooctene, and recovering said at least one isooctene from said reaction product to obtain at least one recovered isooctene. By isooctene is meant any olefin having eight carbons, wherein at least one of the carbons is a secondary or tertiary carbon.

The dry 1-butanol reactant for the process of the invention is derived from fermentation broth. One advantage to the microbial (fermentative) production of butanol is the ability to utilize feedstocks derived from renewable sources, such as corn stalks, corn cobs, sugar cane, sugar beets or wheat, for the fermentation process. Efforts are currently underway to engineer (through recombinant means) or select for organisms that produce butanol with greater efficiency than is obtained with current microorganisms. Such efforts are expected to be successful, and the process of the present invention will be applicable to any fermentation process that produces 1-butanol at levels currently seen with wild-type microorganisms, or with genetically modified microorganisms from which enhanced production of 1-butanol is obtained.

The most well-known method for the microbial production of 1-butanol is the acetone-butanol-ethanol (ABE) fermentation carried out by solventogenic clostridia, such as *Clostridium beijerinickii* or *C. acetobutylicum*. Substrates useful for clostridial fermentation include glucose, maltodextrin and sugars, which may be obtained from biomass, such as corn waste, sugar cane, sugar beets, wheat, hay or straw. A discussion of anaerobiosis and detailed procedures for the preparation of growth media and the growth and storage of anaerobic bacteria (including the sporeforming clostridial species) can be found in Section II of Methods for General and Molecular Bacteriology (Gerhardt, P. et al. (ed.), (1994) American Society for Microbiology, Washington, D.C.). U.S. Pat. No. 6,358,717 (Column 3, line 48 through Column 15, line 21) and U.S. Pat. No. 5,192,673 (Columns 2, line 43 through Column 6, line 57) describe in detail the growth of, and production of 1-butanol by, mutant strains of *C. beijerinckii* and *C. acetobutylicum*, respectively.

An alternative method for the production of 1-butanol by fermentation is a continuous, two-stage process as described in U.S. Pat. No. 5,753,474 (Column 2, line 55 through Column 10, line 67) in which 1-butanol is the major product. In the first stage of the process, a clostridial species, such as *C. tyrobutyricum* or *C. thermobutyricum*, is used to convert a carbohydrate substrate predominantly to butyric acid. In a minor, parallel process, a second clostridial species, such as *C. acetobutylicum* or *C. beijerinkii*, is grown on a carbohydrate substrate under conditions that promote acidogenesis. The butyric acid produced in the first stage is transferred to a second fermentor, along with the second clostridial species, and in the second, solventogenesis stage of the process, the butyric acid is converted by the second clostridial species to 1-butanol.

1-Butanol can also be fermentatively produced by recombinant microorganisms as described in commonly owned 11/527,995 page 3, line 22 through page 48, line 23, including the sequence listing. The biosynthetic pathway enables recombinant organisms to produce a fermentation product comprising 1-butanol from a substrate such as glucose; in addition to 1-butanol, ethanol is formed. The biosynthetic pathway enables recombinant organisms to produce 1-butanol from a substrate such as glucose. The biosynthetic pathway to 1-butanol comprises the following substrate to product conversions:

a) acetyl-CoA to acetoacetyl-CoA, as catalyzed for example by acetyl-CoA acetyltransferase encoded by the genes given as SEQ ID NO:1 or 3;
b) acetoacetyl-CoA to 3-hydroxybutyryl-CoA, as catalyzed for example by 3-hydroxybutyryl-CoA dehydrogenase encoded by the gene given as SEQ ID NO:5;
c) 3-hydroxybutyryl-CoA to crotonyl-CoA, as catalyzed for example by crotonase encoded by the gene given as SEQ ID NO:7;
d) crotonyl-CoA to butyryl-CoA, as catalyzed for example by butyryl-CoA dehydrogenase encoded by the gene given as SEQ ID NO:9;
e) butyryl-CoA to butyraldehyde, as catalyzed for example by butyraldehyde dehydrogenase encoded by the gene given as SEQ ID NO:11; and
f) butyraldehyde to 1-butanol, as catalyzed for example by butanol dehydrogenase encoded by the genes given as SEQ ID NO:13 or 15.

Methods for generating recombinant microorganisms, including isolating genes, constructing vectors, transforming hosts, and analyzing expression of genes of the biosynthetic pathway are described in detail by Donaldson, et al. in U.S. patent application Ser. No. 11/527,995

The biological production of butanol by microorganisms is believed to be limited by butanol toxicity to the host organism. commonly owned U.S. Pat. No. 7,659,104 page 5, line 1 through page 36, Table 5, and including the sequence listing (filed 4 May 2006) enables a method for selecting for microorganisms having enhanced tolerance to butanol, wherein "butanol" refers to 1-butanol, 2-butanol, isobutanol or combinations thereof. A method is provided for the isolation of a butanol tolerant microorganism comprising:

a) providing a microbial sample comprising a microbial consortium;
b) contacting the microbial consortium in a growth medium comprising a fermentable carbon source until the members of the microbial consortium are growing;
c) contacting the growing microbial consortium of step (b) with butanol; and
d) isolating the viable members of step (c) wherein a butanol tolerant microorganism is isolated.

The method of U.S. Pat. No. 7,659,104 can be used to isolate microorganisms tolerant to 1-butanol at levels greater than 1% weight per volume.

Fermentation methodology is well known in the art, and can be carried out in a batch-wise, continuous or semi-continuous manner. As is well known to those skilled in the art, the concentration of 1-butanol in the fermentation broth produced by any process will depend on the microbial strain and the conditions, such as temperature, growth medium, mixing and substrate, under which the microorganism is grown.

Following fermentation, the fermentation broth from the fermentor is subjected to a refining process to recover a stream comprising dry 1-butanol. By "refining process" is meant a process comprising one unit operation or a series of unit operations that allows for the purification of an impure aqueous stream comprising 1-butanol to yield a stream comprising dry 1-butanol.

Typically, refining processes will utilize one or more distillation steps as a means for producing a dry 1-butanol stream. It is well known, however, that fermentative processes typically produce 1-butanol at very low concentrations. This can lead to large capital and energy expenditures to recover the 1-butanol by distillation alone. As such, other techniques can be used in combination with distillation as a means of recovering the 1-butanol. In such processes where separation techniques are integrated with the fermentation step, cells are often removed from the stream to be refined by centrifugation or membrane separation techniques, yielding a clarified fermentation broth. The removed cells are then returned to the fermentor to improve the productivity of the 1-butanol fermentation process. The clarified fermentation broth is then subjected to such techniques as pervaporation, gas stripping, liquid-liquid extraction, perstraction, adsorption, distillation or combinations thereof. The streams generated by these methods can then be treated further by distillation to yield a dry 1-butanol stream.

Distillation

In the ABE fermentation, acetone and ethanol are produced in addition to 1-butanol. The recovery of a butanol stream from an ABE fermentation is well known, and is described, for example, by D. T. Jones (in Clostridia, John Wiley & Sons, New York, 2001, page 125) or by Lenz, T. G. and Moreira, A. R. (Ind. Eng. Chem. Prod. Res. Dev. (1980)19:478-483). Fermentation broth is first fed to a beer still. A vapor stream comprising a mixture of 1-butanol, acetone, ethanol and water is recovered from the top of the column, while a mixture comprising water and cell biomass is removed from the bottom of the column. The vapor stream is subjected to one distillation step or a series of distillation steps, by which acetone and ethanol are separated, and a stream comprising dry 1-butanol is obtained. This dry 1-butanol stream can then be used as the reactant for the process of the present invention.

For fermentation processes in which 1-butanol is the predominant alcohol of the fermentation broth (see U.S. Pat. No. 5,753,474 as described above), dry 1-butanol can be recovered by azeotropic distillation, as described generally in Ramey, D. and Yang, S.-T. (*Production of butyric acid and butanol from biomass*, Final Report of work performed under U.S. Department of Energy DE-F-G02-00ER86106, pages 57-58) for the production of 1-butanol. The aqueous butanol stream from the fermentation broth is fed to a distillation column, from which the butanol-water azeotrope is removed as a vapor phase. The vapor phase from the distillation column (comprising at least about 42% water (by weight relative to the weight of water plus 1-butanol)) can then be fed to a condenser. Upon cooling, a butanol-rich phase (comprising approximately 80% 1-butanol (by weight relative to the weight of water plus 1-butanol)) will separate from a water-rich phase in the condenser. One skilled in the art will know that solubility is a function of temperature, and that the actual concentration of water in the aqueous 1-butanol stream will vary with temperature. The butanol-rich phase can be decanted and sent to a distillation column whereby butanol is separated from water. The dry 1-butanol stream obtained from this column can then be used as the reactant for the process of the present invention.

For fermentation processes in which an aqueous stream comprising 1-butanol and ethanol are produced, without significant quantities of acetone, the aqueous 1-butanol/ethanol stream is fed to a distillation column, from which a ternary 1-butanol/ethanol/water azeotrope is removed. The azeotrope of 1-butanol, ethanol and water is fed to a second distillation column from which an ethanol/water azeotrope is removed as an overhead stream. A stream comprising 1-butanol, water and some ethanol is then cooled and fed to a decanter to form a butanol-rich phase and a water-rich phase. The butanol-rich phase is fed to a third distillation column to separate a dry 1-butanol stream from an ethanol/water stream. The dry 1-butanol stream obtained from this column can then be used as the reactant for the process of the present invention Pervaporation Generally, there are two steps involved in the removal of volatile components by pervaporation. One is the sorption of the volatile component into a membrane, and the other is the diffusion of the volatile component through the membrane due to a concentration gradient. The concentration gradient is created either by a vacuum applied to the opposite side of the membrane or through the use of a sweep gas, such as air or carbon dioxide, also applied along the backside of the membrane. Pervaporation for the separation of 1-butanol from a fermentation broth has been described by Meagher, M. M., et al in U.S. Pat. No. 5,755,967 (Column 5, line 20 through Column 20, line 59) and by Liu, F., et al (Separation and Purification Technology (2005) 42:273-282). According to U.S. Pat. No. 5,755,967, acetone and/or 1-butanol were selectively removed from an ABE fermentation broth using a pervaporation membrane comprising silicalite particles embedded in a polymer matrix. Examples of polymers include polydimethylsiloxane and cellulose acetate, and vacuum was used as the means to create the concentration gradient. A stream comprising 1-butanol and water will be recovered from this process, and this stream can be further treated by distillation to produce a dry 1-butanol stream that can be used as the reactant of the present invention.

Gas Stripping

In general, gas stripping refers to the removal of volatile compounds, such as butanol, from fermentation broth by passing a flow of stripping gas, such as carbon dioxide, helium, hydrogen, nitrogen, or mixtures thereof, through the fermentor culture or through an external stripping column to form an enriched stripping gas. Gas stripping to remove 1-butanol from an ABE fermentation has been exemplified by Ezeji, T., et al (U.S. Patent Application No. 2005/0089979, paragraphs 16 through 84). According to U.S. 2005/0089979, a stripping gas (carbon dioxide and hydrogen) was fed into a fermentor via a sparger. The flow rate of the stripping gas through the fermentor was controlled to give the desired level of solvent removal. The flow rate of the stripping gas is dependent on such factors as configuration of the system, cell concentration and solvent concentration in the fermentor. An enriched stripping gas comprising 1-butanol and water will be recovered from this process, and this stream can be further treated by distillation to produce a dry 1-butanol stream that can be used as the reactant of the present invention.

Adsorption

Using adsorption, organic compounds of interest are removed from dilute aqueous solutions by selective sorption of the organic compound by a sorbant, such as a resin. Feldman, J. in U.S. Pat. No. 4,450,294 (Column 3, line 45 through Column 9, line 40 (Example 6)) describes the recovery of an oxygenated organic compound from a dilute aqueous solution with a cross-linked polyvinylpyridine resin or nuclear substituted derivative thereof. Suitable oxygenated organic compounds included ethanol, acetone, acetic acid, butyric acid, n-propanol and n-butanol. The adsorbed compound was desorbed using a hot inert gas such as carbon dioxide. An aqueous stream comprising desorbed 1-butanol can be recovered from this process, and this stream can be further treated by distillation to produce a dry 1-butanol stream that can be used as the reactant of the present invention.

Liquid-Liquid Extraction

Liquid-liquid extraction is a mass transfer operation in which a liquid solution (the feed) is contacted with an immiscible or nearly immiscible liquid (solvent) that exhibits preferential affinity or selectivity towards one or more of the components in the feed, allowing selective separation of said one or more components from the feed. The solvent comprising the one or more feed components can then be separated, if necessary, from the components by standard techniques, such as distillation or evaporation. One example of the use of liquid-liquid extraction for the separation of butyric acid and butanol from microbial fermentation broth has been described by Cenedella, R. J. in U.S. Pat. No. 4,628,116 (Column 2, line 28 through Column 8, line 57). According to U.S. Pat. No. 4,628,116, fermentation broth containing butyric acid and/or butanol was acidified to a pH from about 4 to about 3.5, and the acidified fermentation broth was then introduced into the bottom of a series of extraction columns containing vinyl bromide as the solvent. The aqueous fermentation broth, being less dense than the vinyl bromide, floated to the top of the column and was drawn off. Any butyric acid and/or butanol present in the fermentation broth was extracted into the vinyl bromide in the column. The column was then drawn down, the vinyl bromide was evaporated, resulting in purified butyric acid and/or butanol.

Other solvent systems for liquid-liquid extraction, such as decanol, have been described by Roffler, S. R., et al. (Bioprocess Eng. (1987) 1:1-12) and Taya, M., et al (J. Ferment. Technol. (1985) 63:181). In these systems, two phases were formed after the extraction: an upper less dense phase comprising decanol, 1-butanol and water, and a more dense phase comprising mainly decanol and water. Aqueous 1-butanol was recovered from the less dense phase by distillation.

These processes are believed to produce an aqueous 1-butanol stream that can be further treated by distillation to produce a dry 1-butanol stream that can be used as the reactant of the present invention.

Dry 1-butanol streams as obtained by any of the above methods can be the reactant for the process of the present invention. The reaction to form at least one isooctene is performed at a temperature of from about 50 degrees Centigrade to about 450 degrees Centigrade. In a more specific embodiment, the temperature is from about 100 degrees Centigrade to about 250 degrees Centigrade.

The reaction can be carried out under an inert atmosphere at a pressure of from about atmospheric pressure (about 0.1 MPa) to about 20.7 MPa. In a more specific embodiment, the pressure is from about 0.1 MPa to about 3.45 MPa. Suitable inert gases include nitrogen, argon and helium.

The reaction can be carried out in liquid or vapor phase and can be run in either batch or continuous mode as described, for example, in H. Scott Fogler, (*Elements of Chemical Reaction Engineering*, $2^{nd}$ Edition, (1992) Prentice-Hall Inc, CA).

The at least one acid catalyst can be a homogeneous or heterogeneous catalyst. Homogeneous catalysis is catalysis in which all reactants and the catalyst are molecularly dispersed in one phase. Homogeneous acid catalysts include, but are not limited to inorganic acids, organic sulfonic acids, heteropolyacids, fluoroalkyl sulfonic acids, metal sulfonates, metal trifluoroacetates, compounds thereof and combinations thereof. Examples of homogeneous acid catalysts include sulfuric acid, fluorosulfonic acid, phosphoric acid, p-toluenesulfonic acid, benzenesulfonic acid, hydrogen fluoride, phosphotungstic acid, phosphomolybdic acid, and trifluoromethanesulfonic acid.

Heterogeneous catalysis refers to catalysis in which the catalyst constitutes a separate phase from the reactants and products. Heterogeneous acid catalysts include, but are not limited to 1) heterogeneous heteropolyacids (HPAs), 2) natural clay minerals, such as those containing alumina or silica, 3) cation exchange resins, 4) metal oxides, 5) mixed metal oxides, 6) metal salts such as metal sulfides, metal sulfates, metal sulfonates, metal nitrates, metal phosphates, metal phosphonates, metal molybdates, metal tungstates, metal borates, and 7) zeolites, 8) combinations of groups 1-7. See, for example, Solid Acid and Base Catalysts, pages 231-273 (Tanabe, K., in Catalysis: Science and Technology, Anderson, J. and Boudart, M (eds.) 1981 Springer-Verlag, New York) for a description of solid catalysts.

The heterogeneous acid catalyst may also be supported on a catalyst support. A support is a material on which the acid catalyst is dispersed. Catalyst supports are well known in the art and are described, for example, in Satterfield, C. N. (Heterogeneous Catalysis in Industrial Practice, $2^{nd}$ Edition, Chapter 4 (1991) McGraw-Hill, New York).

One skilled in the art will know that conditions, such as temperature, catalytic metal, support, reactor configuration and time can affect the reaction kinetics, product yield and product selectivity. Depending on the reaction conditions, such as the particular catalyst used, products other than isooctenes may be produced when 1-butanol is contacted with an acid catalyst. Additional products comprise dibutyl ethers (such as di-1-butyl ether) and butenes. Standard experimentation, performed as described in the Examples herein, can be used to optimize the yield of isooctenes from the reaction.

Following the reaction, if necessary, the catalyst can be separated from the reaction product by any suitable technique known to those skilled in the art, such as decantation, filtration, extraction or membrane separation (see Perry, R. H. and Green, D. W. (eds), Perry's Chemical Engineer's Handbook, $7^{th}$ Edition, Section 13, 1997, McGraw-Hill, New York, Sections 18 and 22).

The at least one isooctene can optionally be recovered from the reaction product by distillation as described in Seader, J. D., et al (Distillation, in Perry, R. H. and Green, D. W. (eds), Perry's Chemical Engineer's Handbook, $7^{th}$ Edition, Section 13, 1997, McGraw-Hill, New York). Alternatively, the at least one isooctene can be recovered by phase separation, or extraction with a suitable solvent, such as trimethylpentane or octane, as is well known in the art. Unreacted 1-butanol can be recovered following separation of the at least one isooctene and used in subsequent reactions.

The present process and certain embodiments for accomplishing it are shown in greater detail in the Drawing figures.

Figure 1:
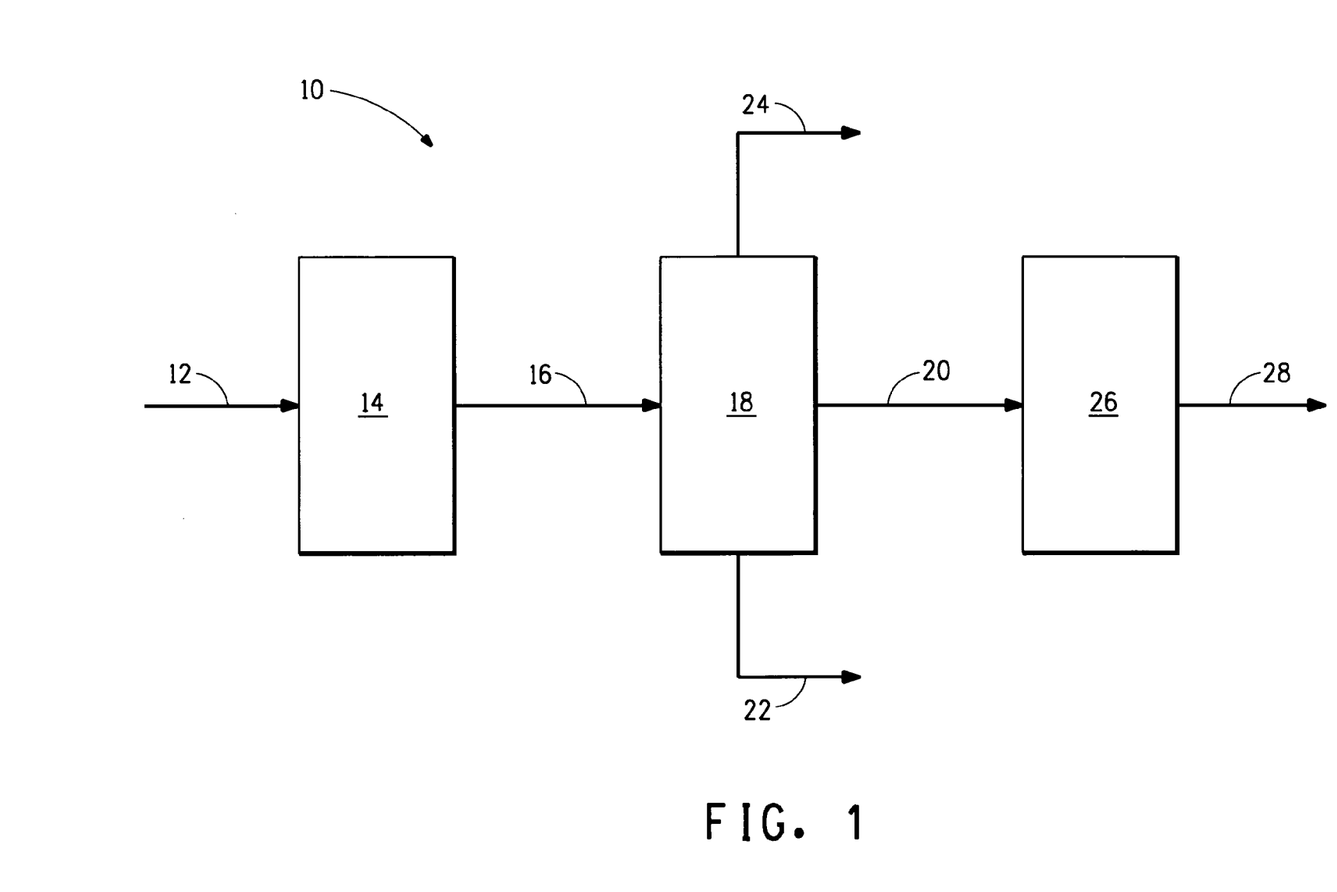
FIG. 1 illustrates an overall process useful for carrying out the present invention.

Referring now to FIG. 1, there is shown a block diagram for apparatus 10 for making at least one isooctene from 1-butanol produced by fermentation. An aqueous stream 12 of biomass-derived carbohydrates is introduced into a fermentor 14. The fermentor 14 contains at least one microorganism (not shown) capable of fermenting the carbohydrates to produce a fermentation broth that comprises 1-butanol and water. A stream 16 of the fermentation broth is introduced into a refining apparatus 18 in order to make a stream of 1-butanol. Dry 1-butanol is removed from the refining apparatus 18 as stream 20. Water is removed from the refining apparatus 18 as stream 22. Other organic components present in the fermentation broth may be removed as stream 24. The 1-butanol-containing stream 20 is introduced into reaction vessel 26 containing an acid catalyst (not shown) capable of converting the 1-butanol into at least one isooctene, which is removed as stream 28.

Figure 2:
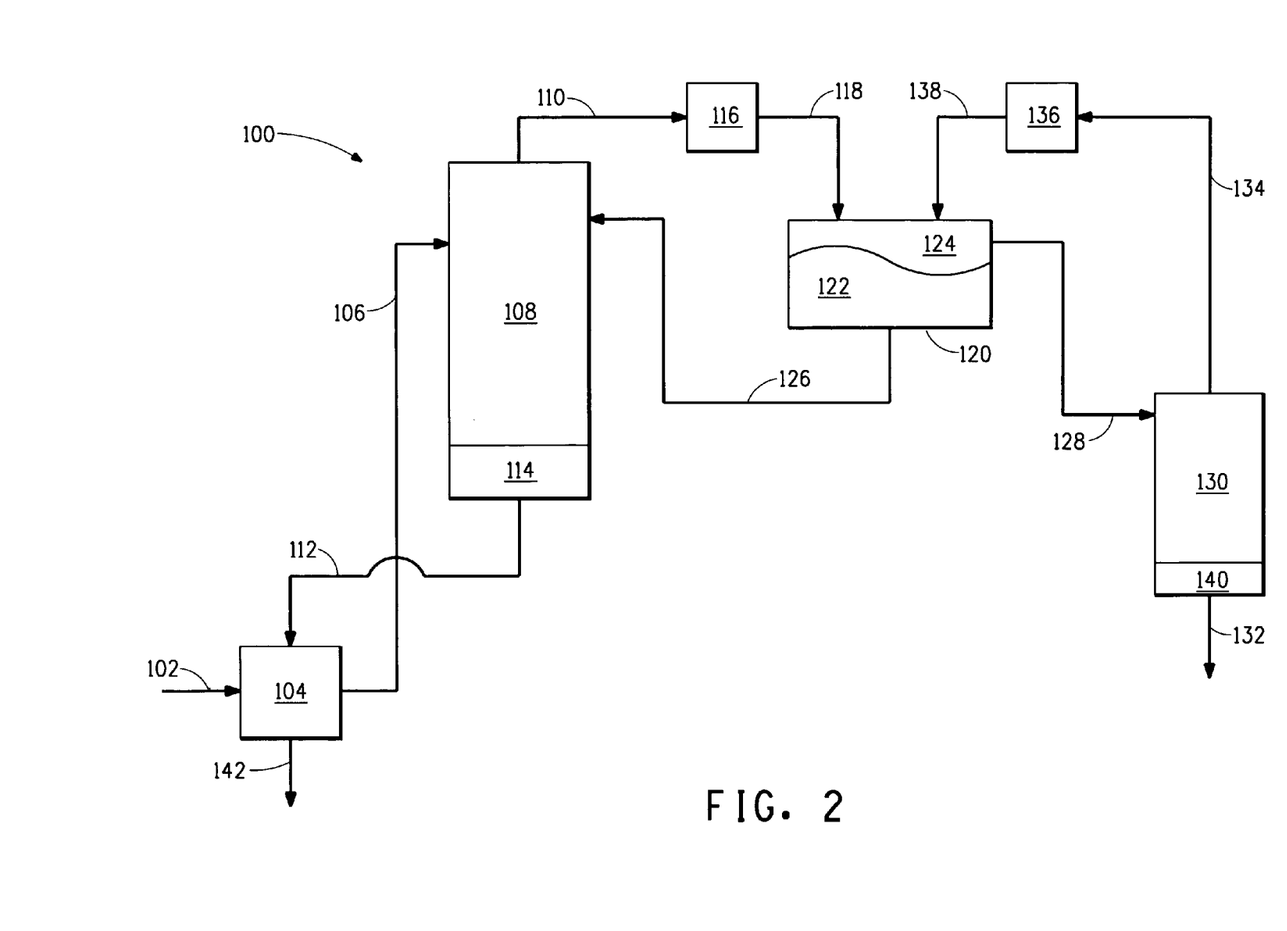
FIG. 2 illustrates a method for producing dry 1-butanol using distillation wherein fermentation broth comprising 1-butanol, but being substantially free of acetone and ethanol, is used as the feed stream.

Referring now to FIG. 2, there is shown a block diagram for refining apparatus 100, suitable for producing a dry 1-butanol stream, when the fermentation broth comprises 1-butanol and water, and is substantially free of acetone and ethanol. A stream 102 of fermentation broth is introduced into a feed preheater 104 to raise the broth to a temperature of approximately 95° C. to produce a heated feed stream 106 which is introduced into a beer column 108. The design of the beer column 108 needs to have a sufficient number of theoretical stages to cause separation of 1-butanol from water such that a 1-butanol water azeotrope can be removed as an overhead stream 110 and a hot water bottoms stream 112. Bottoms stream 112, is used to supply heat to feed preheater 104 and leaves feed preheater 104 as a lower temperature bottoms stream 142. Reboiler 114 is used to supply heat to beer column 108. Overhead stream 110 is fed to a condenser 116, which lowers the stream temperature causing the vaporous overhead stream 110 to condense into a biphasic liquid stream 118, which is introduced into decanter 120. Decanter 120 will contain a lower phase 122 that is approximately 92% by weight water and approximately 8% by weight 1-butanol and an upper phase 124 that is about 82% by weight 1-butanol and about 18% by weight water. A reflux stream 126 of lower phase 122 is introduced near the top of beer column 108. A stream 128 of upper phase 124 is introduced near the top of a butanol separation column 130. Butanol separation column 130 is a standard distillation column having a sufficient number of theoretical stages to allow dry 1-butanol to be recovered as a bottoms product steam 132 and overhead product stream 134 comprising an azeotrope of 1-butanol and water that is fed into condenser 136 to liquefy it to form stream 138, which is reintroduced into decanter 120. Butanol separation column 130 should contain reboiler 140 to supply heat to the column. Stream 132 can then be used as the feed stream to a reaction vessel (not shown) in which the 1-butanol is catalytically converted to a reaction product that comprises at least one isooctene.

Figure 3:
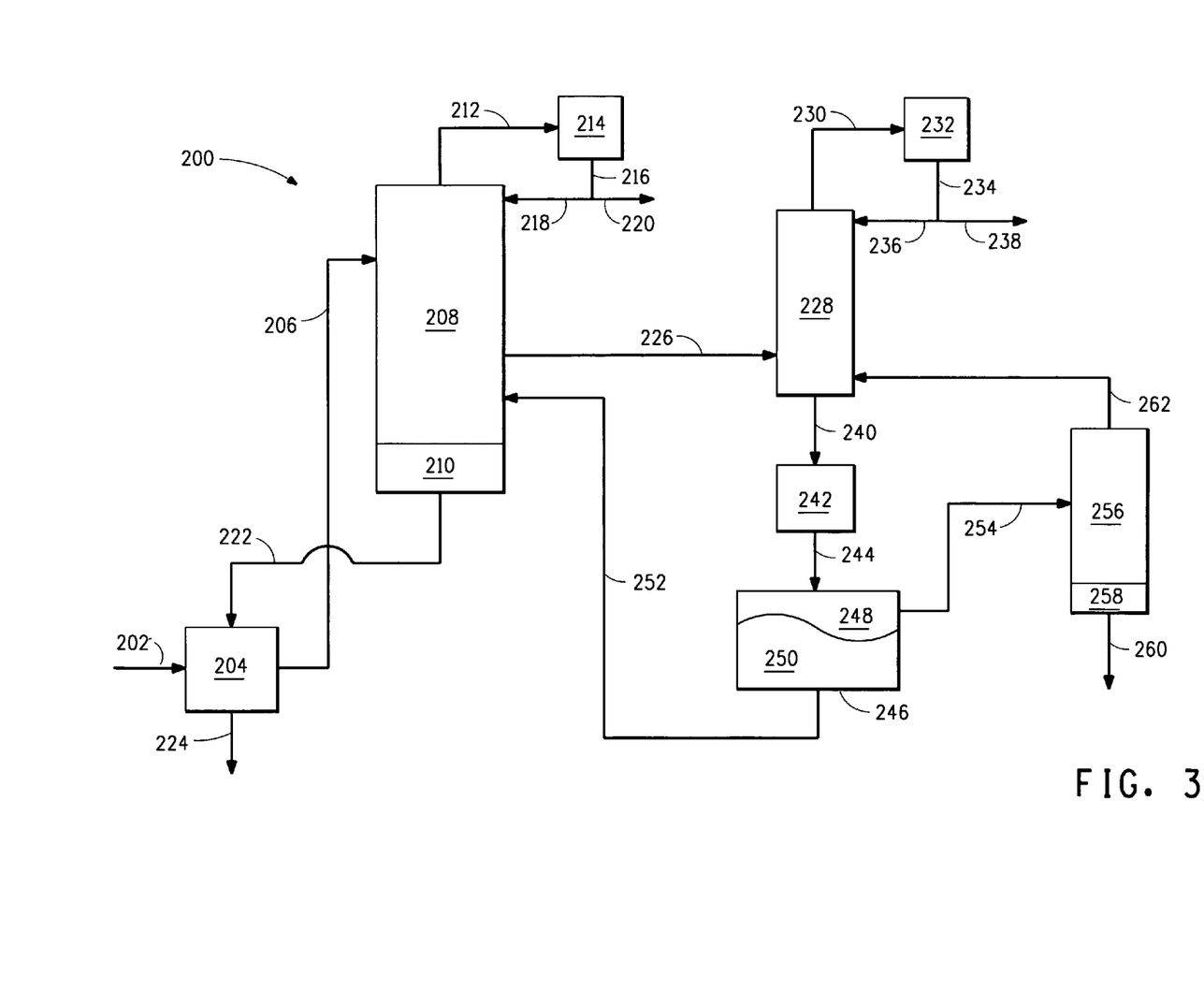
FIG. 3 illustrates a method for producing dry 1-butanol using distillation wherein fermentation broth comprising 1-butanol, ethanol and acetone is used as the feed stream.

Referring now to FIG. 3, there is shown a block diagram for refining apparatus 200, suitable for separating 1-butanol from water, when the fermentation broth comprises 1-butanol, ethanol, acetone, and water. A stream 202 of fermentation broth is introduced into a feed preheater 204 to raise the broth to a temperature of 95° C. to produce a heated feed stream 206 which is introduced into a beer column 208. Beer column 208 is equipped with reboiler 210 necessary to supply heat to the column. The design of the beer column 208 needs to have a sufficient number of theoretical stages to cause separation of acetone from a mixture of 1-butanol, ethanol, acetone and water. Leaving the top of beer column 208 is a vaporous acetone stream 212. Vaporous acetone stream 212 is then fed to condenser 214 where it is fully condensed from a vapor phase to a liquid phase. Leaving condenser 214 is liquid acetone stream 216. Liquid acetone stream 216 is then split into fractions. A first fraction of liquid acetone stream 216 is returned to the top of beer column 208 as acetone reflux stream 218. Liquid acetone product stream 220 is obtained as a second fraction of liquid acetone stream 216. Leaving the bottom of beer column 208 is hot water bottoms stream 222. Hot water bottoms stream 222 is used to supply heat to feed preheater 204 and leaves as lower temperature bottoms stream 224. Also leaving beer column 208 is vaporous side draw stream 226. Vaporous side draw stream 226 contains a mixture of ethanol, butanol, and water. Vaporous side draw stream 226 is then fed to ethanol rectification column 228 in such a manner as to supply both vapor feed stream to the column and necessary heat to drive the separation of butanol from ethanol. Ethanol rectification column 228 contains a sufficient number of theoretical stages to effect the separation of ethanol as vaporous ethanol overhead stream 230 from biphasic butanol bottoms stream 240 containing butanol and water. Vaporous overhead ethanol stream 230 is then fed to condenser 232 where it is fully condensed from a vapor phase to a liquid phase. Leaving condenser 232 is liquid ethanol stream 234. Liquid ethanol stream 234 is then split into fractions. A first fraction of liquid ethanol stream 234 is returned to the top of ethanol rectification column 228 as ethanol reflux stream 236. Liquid ethanol product stream 238 is obtained as a second fraction of liquid ethanol stream 234. Biphasic butanol bottoms stream 240 is then fed to cooler 242 where the temperature is lowered to ensure complete phase separation. Leaving cooler 242 is cooled bottoms stream 244 which is then introduced into decanter 246 where the butanol rich phase 248 is allowed to phase separate from water rich phase 250. The water rich phase stream 252 leaving decanter 246 is returned to beer column 208 below side draw stream 226. The butanol rich stream 254 is fed to butanol column 256. Butanol column 256 is equipped with reboiler 258 necessary to supply heat to the column. Butanol column 256 is equipped with a sufficient amount of theoretical stages to produce a dry butanol bottoms stream 260 and a butanol-water azeotrope overhead stream 262 that is returned to the bottom of ethanol rectification column 228. Bottoms stream 260 can then be used as the feed stream to a reaction vessel (not shown) in which the dry 1-butanol is catalytically converted to a reaction product that comprises at least one isooctene.

Figure 4:
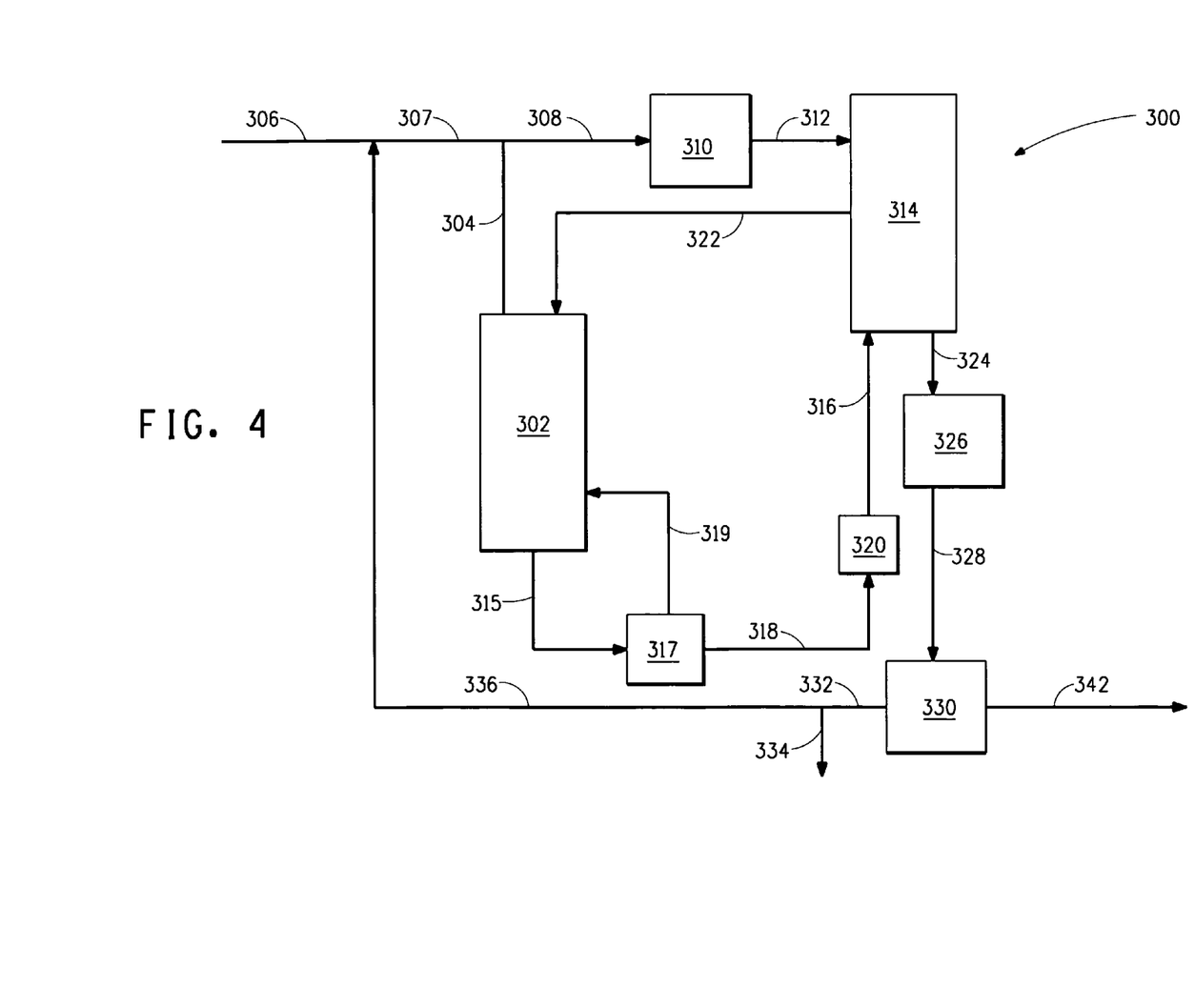
FIG. 4 illustrates a method for producing a 1-butanol/water stream using gas stripping wherein fermentation broth comprising 1-butanol and water is used as the feed stream.

Referring now to FIG. 4, there is shown a block diagram for refining apparatus 300, suitable for concentrating 1-butanol when the fermentation broth comprises 1-butanol and water, and may additionally comprise acetone and/or ethanol. Fermentor 302 contains a fermentation broth comprising liquid 1-butanol and water and a gas phase comprising $CO_2$ and to a lesser extent some vaporous butanol and water. Both phases may additionally comprise acetone and/or ethanol. A $CO_2$ stream 304 is then mixed with combined $CO_2$ stream 307 to give second combined $CO_2$ stream 308. Second combined $CO_2$ stream 308 is then fed to heater 310 and heated to 60° C. to give heated $CO_2$ stream 312. Heated $CO_2$ stream is then fed to gas stripping column 314 where it is brought into contact with heated clarified fermentation broth stream 316. Heated clarified fermentation broth stream 316 is obtained as a clarified fermentation broth stream 318 from cell separator 317 and heated to 50° C. in heater 320. Clarified fermentation broth stream 318 is obtained following separation of cells in cell separator 317. Also leaving cell separator 317 is concentrated cell stream 319 which is recycled directly to fermentor 302. The feed stream 315 to cell separator 317 comprises the liquid phase of fermentor 302. Gas stripping column 314 contains a sufficient number of theoretical stages necessary to effect the transfer of butanol from the liquid phase to the gas phase. The number of theoretical stages is dependent on the contents of both streams 312 and 316, as well as their flow rates and temperatures. Leaving gas stripping column 314 is a butanol depleted clarified fermentation broth stream 322 that is recirculated to fermentor 302. A butanol enriched gas stream 324 leaving gas stripping column 314 is then fed to compressor 326 where it is compressed to 157 kPa (7 psig). Following compression a compressed gas stream comprising butanol 328 is then fed to condenser 330 where the butanol in the gas stream is condensed into a liquid phase that is separate from non-condensable components in the stream 328. Leaving the condenser 330 is butanol depleted gas stream 332. A first portion of gas stream 332 is bled from the system as bleed gas stream 334, and the remaining second portion of butanol depleted gas stream 332, stream 336, is then mixed with makeup $CO_2$ gas stream 306 to form combined $CO_2$ gas stream 307. The condensed butanol phase in condenser 330 leaves as butanol/water stream 342 and feed to a distillation apparatus that is capable of separating 1-butanol from water, as well as from acetone and/or ethanol that may be present in the stream.

Figure 5:
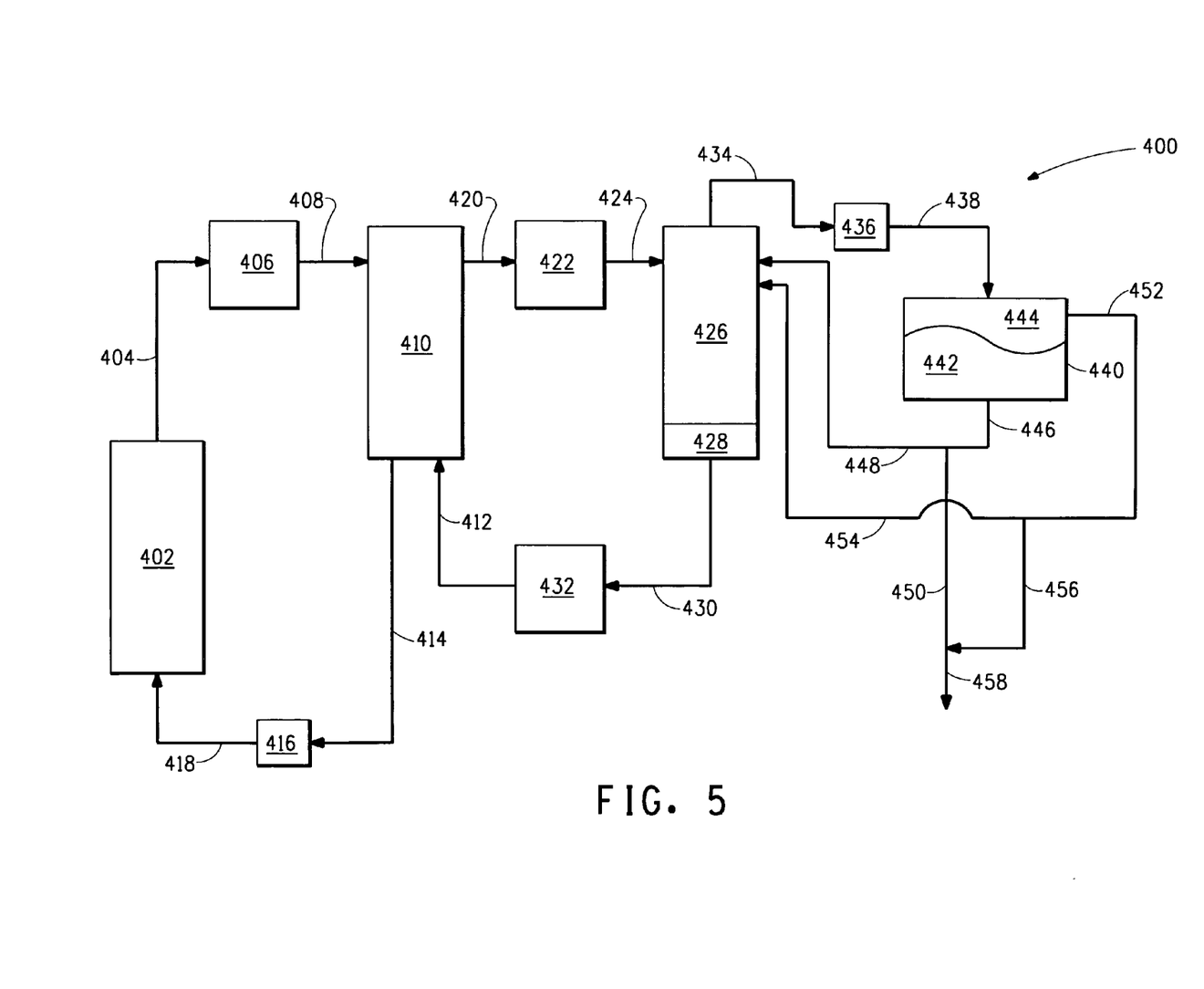
FIG. 5 illustrates a method for producing a 1-butanol/water stream using liquid-liquid extraction wherein fermentation broth comprising 1-butanol and water is used as the feed stream.

Referring now to FIG. 5, there is shown a block diagram for refining apparatus 400, suitable for concentrating 1-butanol, when the fermentation broth comprises 1-butanol and water, and may additionally comprise acetone and/or ethanol. Fermentor 402 contains a fermentation broth comprising 1-butanol and water and a gas phase comprising $CO_2$ and to a lesser extent some vaporous butanol and water. Both phases may additionally comprise acetone and/or ethanol. A stream 404 of fermentation broth is introduced into a feed preheater 406 to raise the broth temperature to produce a heated fermentation broth stream 408 which is introduced into solvent extractor 410. In solvent extractor 410, heated fermentation broth stream 408 is brought into contact with cooled solvent stream 412, the solvent used in this case being decanol. Leaving solvent extractor 410 is raffinate stream 414 that is depleted in butanol. Raffinate stream 414 is introduced into raffinate cooler 416 where it is lowered in temperature and returned to fermentor 402 as cooled raffinate stream 418. Also leaving solvent extractor 410 is extract stream 420 that comprises solvent, butanol and water. Extract stream 420 is introduced into solvent heater 422 where it is heated. Heated extract stream 424 is then introduced into solvent recovery distillation column 426 where the solvent is caused to separate from the butanol and water. Solvent column 426 is equipped with reboiler 428 necessary to supply heat to solvent column 426. Leaving the bottom of solvent column 426 is solvent stream 430. Solvent stream 430 is then introduced into solvent cooler 432 where it is cooled to 50° C. Cooled solvent stream 412 leaves solvent cooler 432 and is returned to extractor 410. Leaving the top of solvent column 426 is solvent overhead stream 434 that contains an azeotropic mixture of butanol and water, with trace amounts of solvent. A solvent overhead stream 434 is then fed into condenser 436, where the vaporous solvent overhead stream is caused to condense into a biphasic liquid stream 438 and introduced into decanter 440. Decanter 440 will contain a lower phase 442 that is approximately 94% by weight water and approximately 6% by weight 1-butanol and an upper phase 444 that is around 80% by weight 1-butanol and about 9% by weight water and a small amount of solvent. The lower phase 442 of decanter 440 leaves decanter 440 as water rich stream 446. Water rich stream 446 is then split into two fractions. A first fraction of water rich stream 446 is returned as water rich reflux stream 448 to solvent column 426. A second fraction of water rich stream 446, water rich product stream 450 is sent on to be mixed with butanol rich stream 456. A stream 452 of upper phase 444 is split into two streams. Stream 454 is fed to solvent column 426 to be used as reflux. Stream 456 is combined with stream 450 to produce product stream 458. Product stream 458 is the result of mixing butanol rich product stream 456 and water rich product stream 450 together. Butanol rich product stream 456 is obtained as a first fraction of butanol rich stream 452. A second fraction of butanol rich stream 452 is returned to the top of solvent column 426 as butanol rich reflux stream 454. Product stream 458 can be introduced as the feed stream to a distillation apparatus that is capable of separating 1-butanol from water, as well as from acetone and/or ethanol that may be present in the stream.

Figure 6:
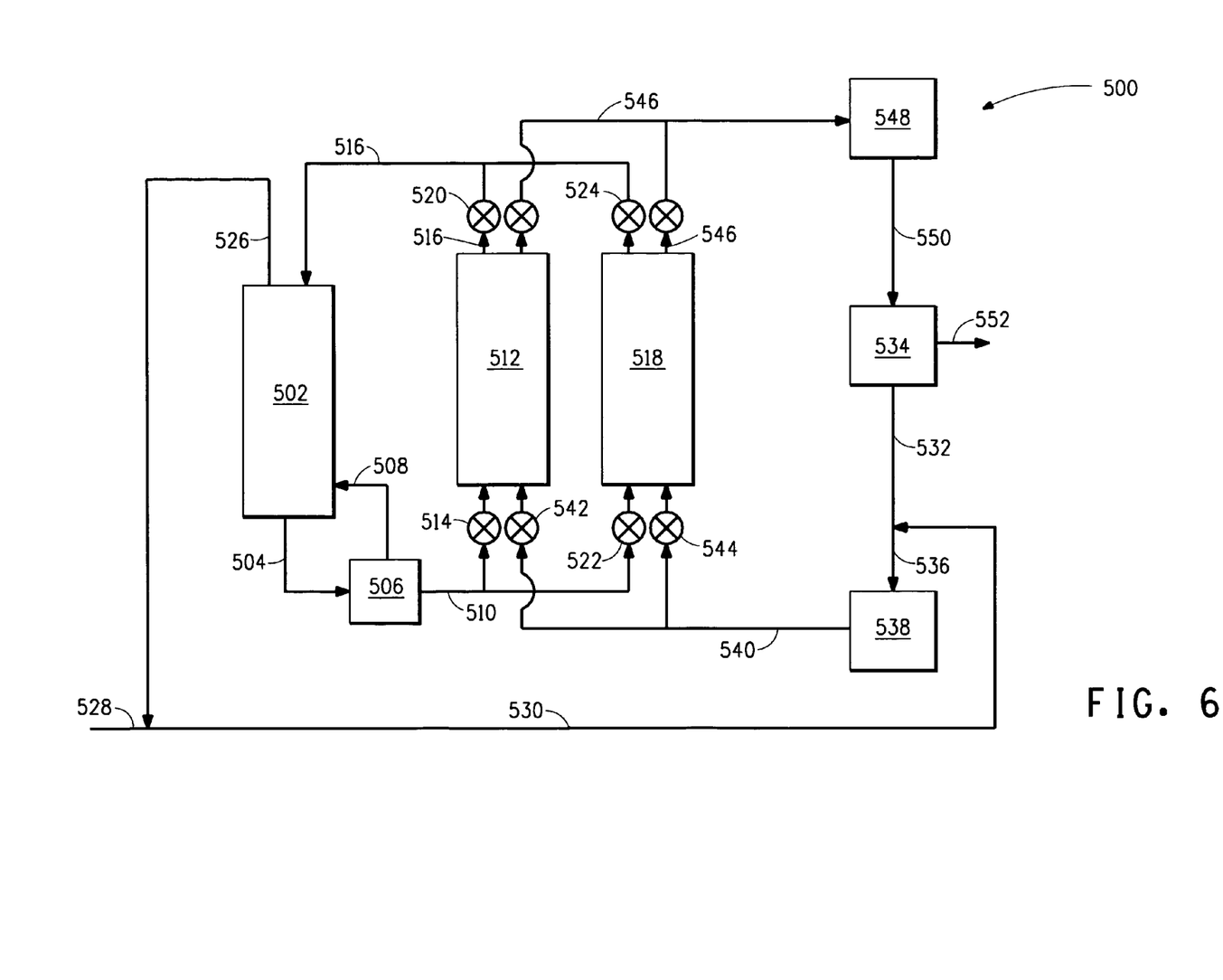
FIG. 6 illustrates a method for producing a 1-butanol/water stream using adsorption wherein fermentation broth comprising 1-butanol and water is used as the feed stream.

Referring now to FIG. 6, there is shown a block diagram for refining apparatus 500, suitable for concentrating 1-butanol, when the fermentation broth comprises 1-butanol and water, and may additionally comprise acetone and/or ethanol. Fermentor 502 contains a fermentation broth comprising 1-butanol and water and a gas phase comprising $CO_2$ and to a lesser extent some vaporous butanol and water. Both phases may additionally comprise acetone and/or ethanol. The butanol containing fermentation broth stream 504 leaving fermentor 502 is introduced into cell separator 506. Cell separator 506 can be comprised of centrifuges or membrane units to accomplish the separation of cells from the fermentation broth. Leaving cell separator 506 is cell containing stream 508 which is recycled back to fermentor 502. Also leaving cell separator 506 is clarified fermentation broth stream 510. Clarified fermentation broth stream 510 is then introduced into one or a series of adsorption columns 512 where the butanol is preferentially removed from the liquid stream and adsorbed on the solid phase adsorbent (not shown). Diagrammatically this is shown in FIG. 6 as a two adsorption column system, although more or fewer columns could be used. The flow of clarified fermentation broth stream 510 is directed to the appropriate adsorption column 512 through the use of switching valve 514. Leaving the top of adsorption column 512 is butanol depleted stream 516 which passes through switching valve 520 and is returned to fermentor 502. When adsorption column 512 reaches capacity, as evidenced by an increase in the butanol concentration of the butanol depleted stream 516, flow of clarified fermentation broth stream 510 is then directed through switching valve 522 by closing switching valve 514. This causes the flow of clarified fermentation broth stream 510 to enter second adsorption column 518 where the butanol is adsorbed on the adsorbent (not shown). Leaving the top of second adsorption column 518 is a butanol depleted stream which is essentially the same as butanol depleted stream 516. Switching valves 520 and 524 perform the function to divert flow of depleted butanol stream 516 from returning to one of the other columns that is currently being desorbed. When either adsorption column 512 or second adsorption column 518 reaches capacity, the butanol and water adsorbed on the adsorbent must be removed. This is accomplished using a heated gas stream to effect desorption of adsorbed butanol and water. The $CO_2$ stream 526 leaving fermentor 502 is first mixed with makeup gas stream 528 to produced combined gas stream 530. Combined gas stream 530 is then mixed with the cooled gas stream 532 leaving decanter 534 to form second combined gas stream 536. Second combined gas stream 536 is then fed to heater 538. Leaving heater 538 is heated gas stream 540 which is diverted into one of the two adsorption columns through the control of switching valves 542 and 544. When passed through either adsorption column 512 or second adsorption column 518, heated gas stream 540 removes the butanol and water from the solid adsorbent. Leaving either adsorption column is butanol/water rich gas stream 546. Butanol/water rich gas stream 546 then enters gas chiller 548 which causes the vaporous butanol and water in butanol/water rich gas stream 546 to condense into a liquid phase that is separate from the other noncondensable species in the stream. Leaving gas chiller 548 is a biphasic gas stream 550 which is fed into decanter 534. In decanter 534 the condensed butanol/water phase is separated from the gas stream. Leaving decanter 534 is butanol and water containing stream 552 which is then fed to a distillation apparatus that is capable of separating 1-butanol from water, as well as from acetone and/or ethanol that may be present in the stream. Also leaving decanter 534 is cooled gas stream 532.

Figure 7:
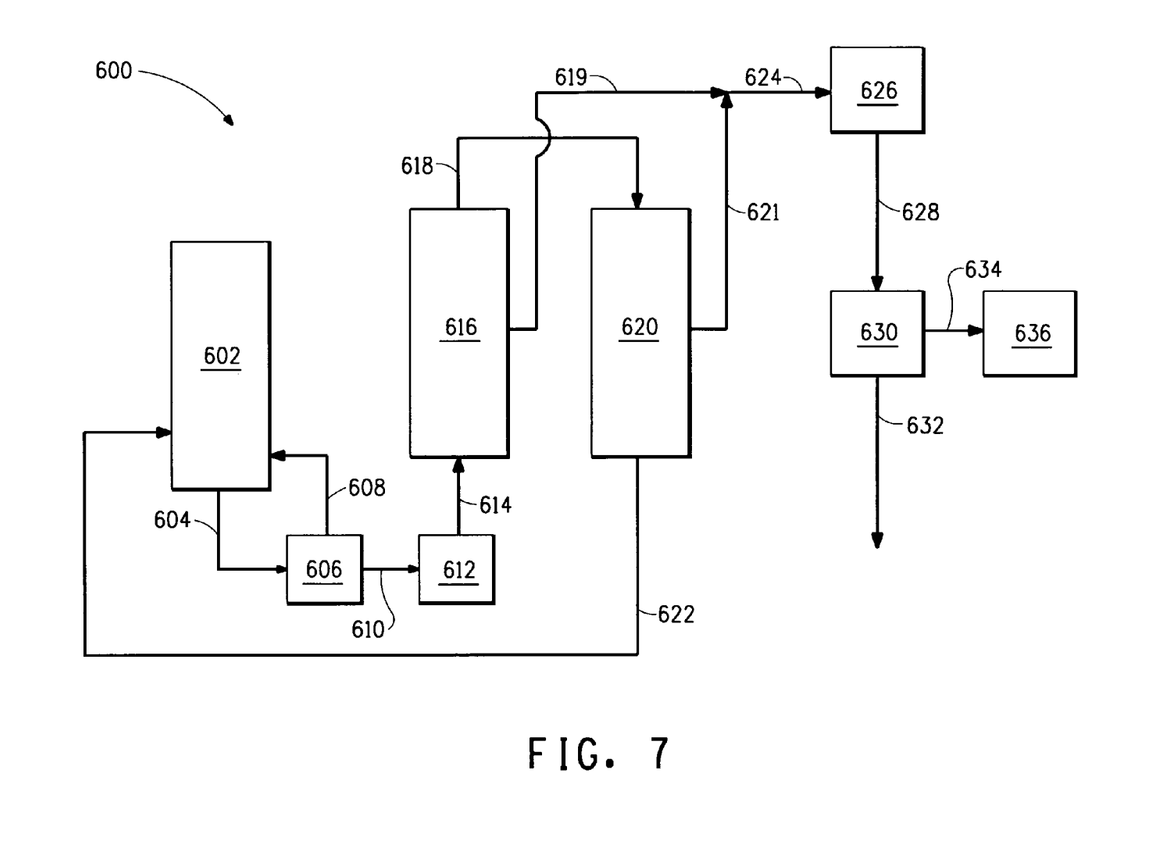
FIG. 7 illustrates a method for producing a 1-butanol/water stream using pervaporation wherein fermentation broth comprising 1-butanol and water is used as the feed stream.

Referring now to FIG. 7, there is shown a block diagram for refining apparatus 600, suitable for concentrating 1-butanol from water, when the fermentation broth comprises 1-butanol and water, and may additionally comprise acetone and/or ethanol. Fermentor 602 contains a fermentation broth comprising 1-butanol and water and a gas phase comprising $CO_2$ and to a lesser extent some vaporous butanol and water. Both phases may additionally comprise acetone and/or ethanol. The butanol containing fermentation broth stream 604 leaving fermentor 602 is introduced into cell separator 606. Butanol-containing stream 604 may contain some non-condensable gas species, such as carbon dioxide. Cell separator 606 can be comprised of centrifuges or membrane units to accomplish the separation of cells from the fermentation broth. Leaving cell separator 606 is concentrated cell stream 608 that is recycled back to fermentor 602. Also leaving cell separator 606 is clarified fermentation broth stream 610. Clarified fermentation broth stream 610 can then be introduced into optional heater 612 where it is optionally raised to a temperature of 40 to 80° C. Leaving optional heater 612 is optionally heated clarified broth stream 614. Optionally heated clarified broth stream 614 is then introduced to the liquid side of first pervaporation module 616. First pervaporation module 616 contains a liquid side that is separated from a low pressure or gas phase side by a membrane (not shown). The membrane serves to keep the phases separated and also exhibits a certain affinity for butanol. In the process of pervaporation any number of pervaporation modules can be used to effect the separation. The number is determined by the concentration of species to be removed and the size of the streams to be processed. Diagrammatically, two pervaporation units are shown in FIG. 7 although any number of units can be used. In first pervaporation module 616 butanol is selectively removed from the liquid phase through a concentration gradient caused when a vacuum is applied to the low pressure side of the membrane. Optionally a sweep gas can be applied to the non-liquid side of the membrane to accomplish a similar purpose. The first depleted butanol stream 618 exiting first pervaporation module 616 then enters second pervaporation module 620. Second butanol depleted stream 622 exiting second pervaporation module 620 is then recycled back to fermentor 602. The low pressure streams 619, 621 exiting both first and second pervaporation modules 616 and 620, respectively, are combined to form low pressure butanol/water stream 624. Low pressure butanol stream 624 is then fed into cooler 626 where the butanol and water in low pressure butanol stream 624 is caused to condense. Leaving cooler 626 is condensed low pressure butanol stream 628. Condensed low pressure butanol stream 628 is then fed to receiver vessel 630 where the condensed butanol/water stream collects and is withdrawn as stream 632. Vacuum pump 636 is connected to the receiving vessel 630 by a connector 634, thereby supplying vacuum to apparatus 600. Non-condensable gas stream 634 exits decanter 630 and is fed to vacuum pump 636. Butanol/water stream 632 is then fed to a distillation apparatus that is capable of separating 1-butanol from water, as well as from acetone and/or ethanol that may be present in the stream.

Figure 8:
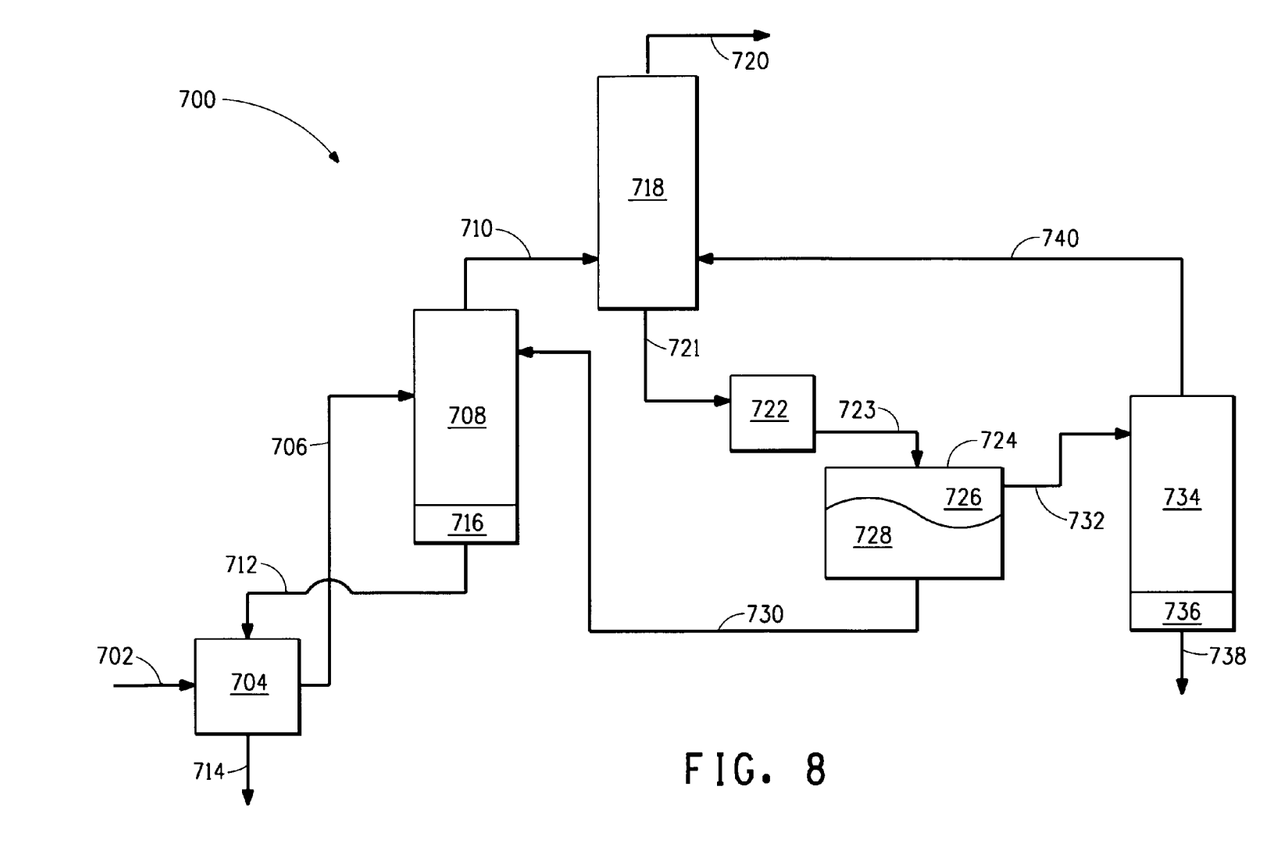
FIG. 8 illustrates a method for producing dry 1-butanol using distillation wherein fermentation broth comprising 1-butanol and ethanol, but being substantially free of acetone, is used as the feed stream.

Referring now to FIG. 8, there is shown a block diagram for refining apparatus 700, suitable for separating 1-butanol from water, when the fermentation broth comprises 1-butanol, ethanol, and water but is substantially free of acetone. A stream 702 of fermentation broth is introduced into a feed preheater 704 to raise the broth temperature to produce a heated feed stream 706 which is introduced into a beer column 708. The beer column 708 needs to have a sufficient number of theoretical stages to cause separation of a ternary azeotrope of 1-butanol, ethanol, and water to be removed as an overhead product stream 710 and a hot water bottoms stream 712. Hot water bottoms stream 712, is used to supply heat to feed preheater 704 and leaves as lower temperature bottoms stream 714. Reboiler 716 is used to supply heat to beer column 708. Overhead stream 710 is a ternary azeotrope of butanol, ethanol and water and is fed to ethanol column 718. Ethanol column 718 contains a sufficient number of theoretical stages to effect the separation of an ethanol water azeotrope as overhead stream 720 and biphasic bottoms stream 721 comprising butanol, ethanol and water. Biphasic bottoms stream 721 is then fed to cooler 722 where the temperature is lowered to ensure complete phase separation. Leaving cooler 722 is cooled bottoms stream 723 which is then introduced into decanter 724 where the butanol rich phase 726 is allowed to phase separate from water rich phase 728. Both phases still contain some amount of ethanol. A water rich phase stream 730 comprising a small amount of ethanol and butanol is returned to beer column 708. A butanol rich stream 732 comprising a small amount of water and ethanol is fed to butanol column 734. Butanol column 734 is equipped with reboiler 736 necessary to supply heat to the column. Butanol column 734 is equipped with a sufficient amount of theoretical stages to produce a dry butanol bottoms stream 738 and an ethanol water azeotropic stream 740 that is returned to ethanol column 718. Dry butanol bottoms stream 738 can then be used as the feed stream to a reaction vessel (not shown) in which the 1-butanol is catalytically converted to a reaction product that comprises at least one isooctene.

The at least one recovered isooctene can be further converted to isooctanes, isooctanols or isooctyl alkyl ethers, which are useful fuel additives. The terms isooctanes and isooctanols are meant to denote eight-carbon compounds having at least one secondary or tertiary carbon. The term isooctyl alkyl ether is meant to denote a compound, the isooctyl moiety of which contains eight carbons, at least one carbon of which is a secondary or tertiary carbon.

In one embodiment of the invention, the at least one isooctene is contacted with at least one hydrogenation catalyst in the presence of hydrogen to produce a reaction product comprising at least one isooctane. Suitable solvents, catalysts, apparatus, and procedures for hydrogenation in general can be found in Augustine, R. L. (Heterogeneous Catalysis for the Synthetic Chemist, Marcel Decker, New York, 1996, Section 3); the hydrogenation can be performed as exemplified in U.S. Patent Application No. 2005/0054861, paragraphs 17-36). In general, the reaction is performed at a temperature of from about 50 degrees Centigrade to about 300 degrees Centigrade, and at a pressure of from about 0.1 MPa to about 20 MPa. The principal component of the hydrogenation catalyst may be selected from metals from the group consisting of palladium, ruthenium, rhenium, rhodium, iridium, platinum, nickel, cobalt, copper, iron, osmium; compounds thereof; and combinations thereof. The catalyst may be supported or unsupported. The at least one isooctane can be separated from the hydrogenation catalyst by any suitable method, including decantation. The at least one isooctane can then be recovered (for example, if the reaction does not go to completion or if a homogeneous catalyst is used) from the reaction product by distillation (see Seader, J. D., supra) to obtain a recovered isooctane, and added to a transportation fuel. Alternatively, the reaction product itself can be added to a transportation fuel. If present, unreacted isooctenes can be used in subsequent reactions to produce isooctanes.

In another embodiment, the at least one isooctene is contacted with water in the presence of at least one acidic catalyst to produce a reaction product comprising at least one isooctanol. The hydration of olefins is well known, and a method to carry out the hydration using a zeolite catalyst is described in U.S. Pat. No. 5,288,924 (Column 3, line 48 to Column 7, line 66), wherein a temperature of from about 60 degrees Centigrade to about 450 degrees Centigrade and a pressure of from about 700 kPa to about 24,500 kPa are used. The water to olefin ratio is from about 0.05 to about 30. Where a solid acid catalyst is used, such as a zeolite, the at least one isooctanol can be separated from the at least one acid catalyst by any suitable method, including decantation. The at least one isooctanol can then be recovered from the reaction product by distillation (see Seader, J. D., supra) to obtain a recovered isooctanol, and added to a transportation fuel. Alternatively, the reaction product itself can be added to a transportation fuel. Unreacted isooctenes, if present, can be used in subsequent reactions to produce isooctanols.

In still another embodiment, the at least one isooctene is contacted with at least one acid catalyst in the presence of at least one straight-chain or branched $C_1$ to $C_5$ alcohol to produce a reaction product comprising at least one isooctyl alkyl ether. One skilled in the art will recognize that $C_1$ and $C_2$ alcohols cannot be branched. The etherification reaction is described by Stüwe, A., et al (Synthesis of MTBE and TAME and related reactions, Section 3.11, in Handbook of Heterogeneous Catalysis, Volume 4, (Ertl, G., Knözinger, H., and Weitkamp, J. (eds), 1997, VCH Verlagsgesellschaft mbH, Weinheim, Germany)) for the production of methyl-t-butyl ether. The etherification reaction is generally carried out at temperature of from about 50 degrees Centigrade to about 200 degrees Centigrade at a pressure of from about 0.1 to about 20.7 MPa. Suitable acid catalysts include, but are not limited to, acidic ion exchange resins. Where a solid acid catalyst is used, such as an ion-exchange resin, the at least one isooctyl alkyl ether can be separated from the at least one acid catalyst by any suitable method, including decantation. The at least one isooctyl alkyl ether can then be recovered from the reaction product by distillation (see Seader, J. D., supra) to obtain a recovered isooctyl alkyl ether, and added to a transportation fuel. If present, unreacted isooctenes can be used in subsequent reactions to produce isooctyl alkyl ethers.

According to embodiments described above, isooctenes produced by the reaction of 1-butanol with at least one acid catalyst are first recovered from the reaction product prior to being converted to compounds useful in transportation fuels. However, as described in the following embodiment, the reaction product comprising isooctenes can also be used in subsequent reactions without first recovering said isooctenes.

Thus, one alternative embodiment of the invention is a process for making at least one isooctane comprising:

(a) obtaining a fermentation broth comprising 1-butanol;

(b) separating dry 1-butanol from said fermentation broth to form separated dry 1-butanol;

(c) contacting the separated dry 1-butanol of step (b), optionally in the presence of a solvent, with at least one acid catalyst at a temperature of about 50 degrees C. to about 450 degrees C. and a pressure from about 0.1 MPa to about 20.7 MPa to produce a first reaction product comprising at least one isooctene;

(d) contacting said first reaction product with hydrogen in the presence of at least one hydrogenation catalyst to produce a second reaction product comprising at least one isooctane; and (e) recovering the at least one isooctane from the second reaction product to produce a recovered isooctane.

The at least one recovered isooctane can then be added to a transportation fuel.

General Methods and Materials

In the following examples, "C" is degrees Centigrade, "mg" is milligram; "ml" is milliliter; "temp" is temperature; "MPa" is mega Pascal; "GC/MS" is gas chromatography/mass spectrometry.

Amberlyst® (manufactured by Rohm and Haas, Philadelphia, Pa.), tungstic acid, 1-butanol and $H_2SO_4$ were obtained from Alfa Aesar (Ward Hill, Mass.); CBV-3020E was obtained from PQ Corporation (Berwyn, Pa.); 13% Nafion®/$SiO_2$ can be obtained from Engelhard; and H-Mordenite can be obtained from Zeolyst Intl. (Valley Forge, Pa.).

General Procedure for the Conversion of 1-Butanol to Isooctenes

A mixture of 1-butanol and catalyst was contained in a 2 ml vial equipped with a magnetic stir bar. The vial was sealed with a serum cap perforated with a needle to facilitate gas exchange. The vial was placed in a block heater enclosed in a pressure vessel. The vessel was purged with nitrogen and the pressure was set at 6.9 MPa. The block was brought to the indicated temperature and controlled at that temperature for the time indicated. After cooling and venting, the contents of the vial were analyzed by GC/MS using a capillary column (either (a) CP-Wax 58 [Varian; Palo Alto, Calif.], 25 m×0.25 mm, 45 C/6 min, 10 C/min up to 200 C, 200 C/10 min, or (b) DB-1701 [J&W (available through Agilent; Palo Alto, Calif.)], 30 m×0.25 mm, 50 C/10 min, 10 C/min up to 250 C, 250 C/2 min).

The examples below were performed according to this procedure under the conditions indicated for each example. "Sel" is selectivity; "Conv" is conversion.

EXAMPLES 1-6

Reaction of 1-Butanol (1-BuOH) with an Acid Catalyst to Produce Isooctenes

The reactions were carried out for 2 hours at 6.9 MPa of $N_2$.

| Example Number | Catalyst | Temp (C.) | 1-BuOH % Conv | Isooctenes % Sel |
|---|---|---|---|---|
| 1 | $H_2SO_4$ | 200 | 93.6 | 0.3 |
| 2 | Amberlyst ® 15 | 200 | 65.8 | 0.2 |
| 3 | 13% Nafion ®/$SiO_2$ | 200 | 39.2 | 0.1 |
| 4 | CBV-3020E | 200 | 86.8 | 0.3 |
| 5 | H-Mordenite | 200 | 69.5 | 4.4 |
| 6 | Tungstic Acid | 200 | 9.3 | 0.2 |

As those skilled in the art of catalysis know, when working with any catalyst, the reaction conditions need to be optimized. Examples 1 to 6 show that the indicated catalysts were capable under the indicated conditions of producing the product isooctenes. Some of the catalysts shown in Examples 1 to 6 were ineffective when utilized at suboptimal conditions (e.g., lower temperature) (data not shown).

The invention claimed is:

1. A process for making at least one isooctene comprising:
    (a) obtaining a fermentation broth comprising recombinant microorganisms and 1-butanol wherein the fermentation broth is substantially free of acetone and ethanol;
    (b) separating dry 1-butanol from said fermentation broth to form separated dry 1-butanol comprising the steps of heating a stream of fermentation broth and introducing the heated stream into a beer column removing from the beer column a 1-butanol water azeotrope and condensing it to a biphasic liquid stream having an upper phase and a lower phase and introducing a stream of the upper phase into a butanol separation column
    (c) contacting the separated dry 1-butanol of step (b), optionally in the presence of a solvent, with at least one acid catalyst at a temperature of about 50 degrees C. to about 450 degrees C. and a pressure from about 0.1 MPa to about 20.7 MPa to produce a reaction product comprising said at least one isooctene; and
    (d) recovering said at least one isooctene from said reaction product to obtain at least one recovered isooctene.

* * * * *